(12) United States Patent
Lee et al.

(10) Patent No.: US 8,670,122 B2
(45) Date of Patent: Mar. 11, 2014

(54) SURFACE PLASMON RESONANCE MEASURING DEVICE

(75) Inventors: Ju-Yi Lee, Taoyuan County (TW); Shin-Kai Tsai, Taoyuan County (TW)

(73) Assignee: National Central University, Taoyuan (TW)

( * ) Notice: Subject to any disclaimer, the term of this patent is extended or adjusted under 35 U.S.C. 154(b) by 581 days.

(21) Appl. No.: 12/952,647

(22) Filed: Nov. 23, 2010

(65) Prior Publication Data

US 2011/0273716 A1    Nov. 10, 2011

(30) Foreign Application Priority Data

May 4, 2010  (TW) ................................ 99114235 A

(51) Int. Cl.
 *G01N 21/55*  (2006.01)
(52) U.S. Cl.
 USPC ......................................................... 356/445
(58) Field of Classification Search
 USPC ........................................................ 356/445
 See application file for complete search history.

(56) References Cited

U.S. PATENT DOCUMENTS 6,628,376 B1 *  9/2003  Nikitin et al. ................... 356/38
2004/0227942 A1 * 11/2004  Law et al. ....................... 356/364

* cited by examiner

*Primary Examiner* — Tarifur Chowdhury
*Assistant Examiner* — Omar Nixon
(74) *Attorney, Agent, or Firm* — Rosenberg, Klein & Lee

(57) ABSTRACT

A SPR measuring device is proposed. The measuring device includes a circularly polarized heterodyne light source that produces a circularly polarized heterodyne light beam, a beam splitting element that splits the circularly polarized heterodyne light beam into a reference beam and a signal beam, a first light sensing unit that receives a reference light intensity of the reference beam, a SPR sensor that receives the signal beam and reflects a reflected signal beam, a second light sensing unit that receives a reflected light intensity of the reflected signal beam and a processing circuit that calculates a phase difference between the reference light intensity and the reflected light intensity. A phase change caused by SPR of an incident light is sensitively represented by the circularly polarized heterodyne light beam. Thus tiny changes in physical quantities of analytes are measured easily.

14 Claims, 7 Drawing Sheets

SURFACE PLASMON RESONANCE MEASURING DEVICE

BACKGROUND OF THE INVENTION

1. Fields of the Invention

The present invention relates to a surface plasmon resonance (SPR) measuring device, especially to a SPR measuring device in which the wavelength of an incident beam from a circularly polarized heterodyne light source can be modulated.

2. Descriptions of Related Art

Biosensors are devices for biomolecular interaction analysis, detecting changes of interface properties caused by a specific interaction between specific molecules and target analytes on the sensor interface. Along with development and integration of electro-optical techniques with micro-electro-mechanical system (MEMS), plurality of biosensing techniques such as confocal laser scanning fluorescence microscopy (CLSFM), Quadtz crystalmicro-balance (QCM), SPR, etc have been developed. SPR has high sensitivity for detection of interface changes and hence has received a great attention from scientists. The SPR properties have been extensively studied and various applications such as biological detections have been developed. SPR instrumentation has been commercialized by a number of companies and SPR techniques have been used for real-time detection of biomolecular reactions.

Since B. Liedberg applied SPR to gas detection and biosensing in 1983, analysis systems based on SPR have been broadly used in various fields. For example, the SPR technique combine with biochips is used in biomedical applications with advantages of label free, immediate detection and high sensitivity. Thus SPR has become a hot topic in research of nano science and biomedical science. SPR is divided into three groups according to the principle of measurement. There are three kinds of SPR detection:

1. angular modulation
2. wavelength modulation
3. phase modulation

The angle of SPR can be determined by using the angular modulation, which is kept constant and the angle of incidence is varied, then the sharp dip appears at a specific angle so as to find out the angle of SPR. As to another method-wavelength modulation, the angle of the incident beam is kept constant and the wavelength is varied. In this method, SPR occurs at a specific wavelength. The SPR parameter (angle or wavelength) depends on the refractive index of the dielectric medium. Change in refractive index changes the value of the SPR parameter. According to changes of the angle and wavelength of SPR, the refractive index or interface bio-reaction is detected. The advantages of the angular or wavelength modulation are a simple structure and an easily-obtained experiment results. But the measurement resolution is not enough. On the other hand, the phase modulation has high measurement resolution. This is due to the phase of the SPR reflected light is highly sensitive to biomolecular interactions at the interface. Although the angular or wavelength modulation is simple and most of SPR equipments are based on these methods, the phase-based detection has become a mainstream because that the concentration of the analyte is much lower and users has higher requirements of the resolution and detection speed.

The SPR phase variation is measured by the heterodyne interferometry, or the phase-shift interferometry (PSI) technique. Refer to a journal article-"Surface plasmon resonance phase shift inter ferometry: Real-time DNA microarray hybridization analysis" (S.-J. Chen*, Y.-D. Su, F.-M. Hsiu, C.-Y. Tsou, and Y.-K. Chen, "Surface plasmon resonance phase shift interferometry: Real-time DNA microarray hybridization analysis," Journal of Biomedical Optics, vol. 10, no 3,034005, May/June 2005.), reported by a research team of Chen, Shean-Jen, SPR-PSI is a novel technique used to measure the spatial phase variation caused by biomolecular interactions upon a sensing chip. The SPR-PSI imaging system has an enhanced detection limit of $2.5 \times 10^{-7}$ refractive index change and a long-time phase stability of $\pi/100$ in 30 minutes. Also refer to Taiwanese Pub. App. No. 555972, dated Oct. 1, 2003, "SPR heterodyne interferometry measuring device and method" by Chien Chou, Wen-Chuan Kuo, and the device can detect 0.2 nM concentration changes. Although these techniques can detect tiny concentration and the refractive index, the instruments are high cost. For example, heterodyne light sources or piezoelectric actuators are required. Take PSI as an example, beside the piezoelectric actuator, the sampling time depends on the movement of the piezoelectric actuator. Thus the method can't be used in real-time measurement. Moreover, the phase shift drifts easily due to environmental change. Thus there is a need to provide a novel device that overcomes shortcomings of the above prior arts.

In order to improve above shortcomings of prior arts, the present invention provides a concept of phase differential detection. By a circularly polarized heterodyne light source generated from wavelength modulation in combination with SPR, a phase differential type of SPR measuring device has been developed.

SUMMARY OF THE INVENTION

Therefore it is a primary object of the present invention to provide a SPR measuring device in which a circularly polarized heterodyne light beam is produced by a circularly polarized heterodyne light source. A phase change caused by SPR of an incident light is sensitively represented by the circularly polarized heterodyne light beam. Thus the convenience of measuring tiny changes in physical quantities of the analyte is improved.

It is another object of the present invention to provide a SPR measuring device, the SPR measuring device includes an optical module so as to obtain twice the phase change of a light signal of an incident light after SPR and the sensitivity of the SPR measurement is improved.

In order to achieve above objects, a SPR measuring device of the present invention consists of a circularly polarized heterodyne light source, a beam splitting element, a first light sensing unit, a SPR sensor, a second light sensing unit, and a processing circuit. The circularly polarized heterodyne light source produces a circularly polarized heterodyne light beam and the beam splitting element splits the circularly polarized heterodyne light beam into a reference beam and a signal beam. The first light sensing unit receives a reference light intensity of the reference beam. The SPR sensor receives the signal beam and reflects a reflected signal beam. The second light sensing unit receives a reflected light intensity of the reflected signal beam and the processing circuit calculates a phase difference between the reference light intensity and the reflected light intensity. According to the circularly polarized heterodyne light beam, a phase change caused by SPR of an incident light is sensitively represented. Thus tiny changes in physical quantities of the analyte are measured easily and conveniently.

The device further includes an optical module that receives the reflected signal beam for amplifying the phase change of the reflected signal beam and transmits the reflected signal beam to the second light sensing unit. Thus twice the phase change of the light signal of the incident light after SPR is obtained and the sensitivity of the SPR measurement is improved.

BRIEF DESCRIPTION OF THE DRAWINGS

The structure and the technique mean adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1A:
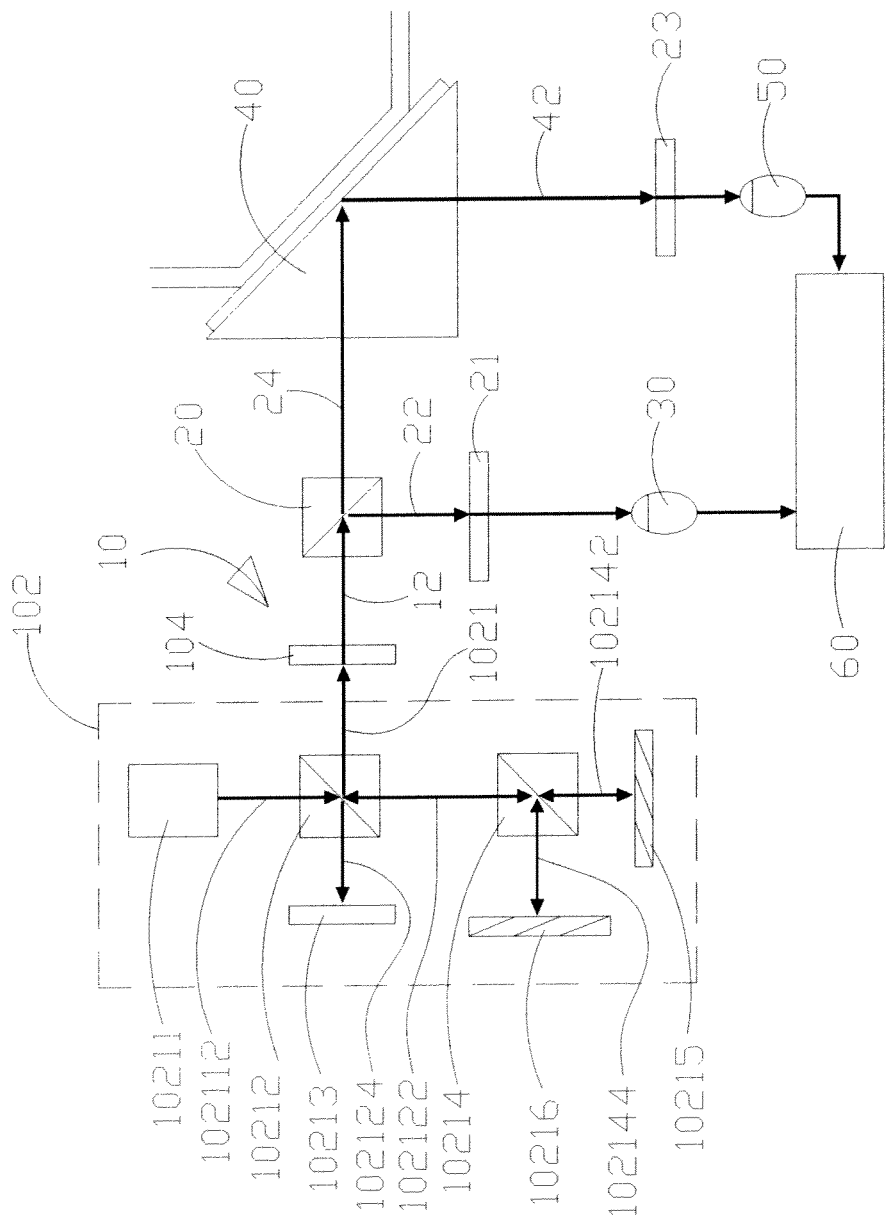
FIG. 1A is a schematic drawing showing structure of an embodiment of a SPR measuring device according to the present invention.

Refer to FIG. 1A, a SPR measuring device consists of a circularly polarized heterodyne light source 10, a beam splitting element 20, a first light sensing unit 30, a SPR sensor 40, a second light sensing unit 50, and a processing circuit 60. The circularly polarized heterodyne light source 10 produces a circularly polarized heterodyne light beam 12 and the beam splitting element 20 splits the circularly polarized heterodyne light beam 12 into a reference beam 22 and a signal beam 24. The first light sensing unit 30 receives a reference light intensity of the reference beam 22. The SPR sensor 40 receives the signal beam 24 and reflects a reflected signal beam 42. The second light sensing unit 50 receives a reflected light intensity of the reflected signal beam 42 and the processing circuit 60 calculates a phase difference between the reference light intensity and the reflected light intensity. The processing circuit 60 includes a lock-in amplifier. By the circularly polarized heterodyne light beam 12, a phase change caused by SPR of an incident light is represented sensitively and the convenience of measuring tiny changes in physical quantities of the analyte is improved.

The circularly polarized heterodyne light source 10 consists of a heterodyne light source 102 and a phase retardation component 104. The heterodyne light source 102 generates (produces) a heterodyne light beam 1021 and the phase retardation component 104 retards the heterodyne light beam 1021 to produce the circularly polarized heterodyne light beam 12. In this embodiment, the phase retardation component 104 used is a quarter-wave plate at 45 degree.

The heterodyne light source 102 consists of a wavelength-modulated light source 10211, a beam splitter 10212, a light shielding element 10213, a polarization beam splitter 10214, a first reflector 10215, and a second reflector 10216. The wavelength-modulated light source 10211 produces an incident beam 102112. The wavelength-modulated light source 10211 used in the present invention is a laser diode. Within the working range, the laser diode emits an incident laser beam 102112 with a center wavelength λ. The wavelength of the incident laser beam 102112 is modulated according to changes of current applied to the laser diode. By sawtooth waves from a function generator, the wavelength from the wavelength-modulated light source 10211 is modulated.

The beam splitter 10212 splits the incident beam 102112 into a first transmitted beam 102122 and a first reflected beam 102124. The light shielding element 10213 receives the first reflected beam 102124 so as to avoid that the reflected beam 102124 is reflected to the beam splitter 10212 and further interfering the heterodyne light beam 1021 formed by superposition of beams.

The polarization beam splitter 10214 splits the first transmitted beam 102122 into a second transmitted beam 102142 and a second reflected beam 102144. The first reflector 10215 reflects the second transmitted beam 102142 back to the polarization beam splitter 10214 while a second reflector 10216 reflects the second reflected beam 102144 back to the polarization beam splitter 10214. Thus the heterodyne light beam 1021 is formed by superposition of the reflected second transmitted beam 102142 and the reflected second reflected beam 102144. The heterodyne light beam 1021 is outputted to the phase retardation component 104 through the beam splitter 10212 so that the heterodyne light beam 1021 becomes the circularly polarized heterodyne light beam 12

The present invention splits the incident beam 102112 into a transmitted P-wave light and a reflected S-wave light by the polarization beam splitter 10214. The P-wave light is the first transmitted beam 102122 and the S-wave light is the first reflected beam 102124. The first reflector 10215 and the second reflector 10216 of the present invention are mirrors. The P-wave light and the S-wave light are reflected by the mirrors back to the polarization beam splitter 10214 and recombined (reunite, superimpose, superposition). Thus the P-wave light and the S-wave light travel along different optical paths. After superposition, the heterodyne light beam 1021 in which the P-wave light and the S-wave light have frequency difference is formed. The heterodyne light beam 1021 changes into the circularly polarized heterodyne light beam 12 through the phase retardation component 104. The electric field form of the circularly polarized heterodyne light beam 12 is represented as:

$$E = \begin{bmatrix} \cos(\omega t/2) \\ \sin(\omega t/2) \end{bmatrix}, \quad (1)$$

wherein $\omega = 2\pi\Delta L \Delta\lambda/\lambda_0^2 T$ is heterodyne beat, $\Delta L$ is the optical path difference between the P-wave light and the S-wave light, λ is center wavelength of the laser diode light source, $\Delta\lambda$ is wavelength modulation depth, T is modulation period.

The circularly polarized heterodyne light beam 12 is split into the reference beam 22 and the signal beam 24 by the beam splitting element 20. The reference beam 22 passes a polarizer 21 with a transmission axis at 45 degree to be received by the first light sensing unit 30 and its light (beam) intensity is mathematically represented as:

$$I_{D1} \propto |E_{D1}|^2 = |P(45°) \cdot E|^2 \quad (2)$$

$$= \left\| \begin{bmatrix} 1 & 1 \\ 1 & 1 \end{bmatrix} \cdot A \cdot \begin{bmatrix} \cos(\omega t/2) \\ \sin(\omega t/2) \end{bmatrix} \right\|$$

$$= DC_1 + AC_1 \sin(\omega t),$$

where $P_1$ is the polarizer 21 and $D_1$ is the first light sensing unit 30.

When the signal beam 24 incidence into the SPR sensor 40 satisfies the resonant conditions, the emergent signal beam 24 passes the polarizer 23 with a transmission axis at 45 degree to be received by the second light sensing unit 50 and its light intensity is mathematically represented as:

$$I_{D2} \propto |E_{D2}|^2 = |P_2(45) \cdot J_{SPR} \cdot E|^2 \quad (3)$$

$$= \left\| \begin{bmatrix} 1 & 1 \\ 1 & 1 \end{bmatrix} \cdot \begin{bmatrix} |r_P|e^{i\phi_P} & 0 \\ 0 & |r_S|e^{i\phi_S} \end{bmatrix} \cdot A \cdot \begin{bmatrix} \cos(\omega t/2) \\ \sin(\omega t/2) \end{bmatrix} \right\|$$

$$= DC_2 + AC_2 \sin(\omega t + \Phi),$$

$$\Phi = \tan^{-1} \frac{2|r_P||r_S|\cos(\phi_P - \phi_S)}{|r_P|^2 - |r_S|^2}, \quad (4)$$

where $r_P$, $r_S$ are reflectance of P-wave light and S-wave light, respectively. $\theta_P$, $\theta_S$ are the phase of P-wave light and S-wave light, $P_2$ is the polarizer 23, and $D_2$ is the second light sensing unit 50.

$DC_1$, $AC_1$, $DC_2$, and $AC_2$ in the equation (2) and the equation (3) are DC components and AC components of the light intensity. $\Phi$ is the phase difference since the circularly polarized heterodyne light beam passing the SPR sensor 40. The wavelength of laser diode is modulated by sawtooth waves and its light intensity is also in sawtooth wave form and is expressed as I(t). Thus the light intensity is modified as follows:

$$I_{D1} = I(t) \times [DC_1 + AC_1 \sin(\omega t)], \quad (5)$$

$$I_{D2} = I(t) \times [DC_2 + AC_2 \sin(\omega t + \Phi)]. \quad (6)$$

Figure 1B:
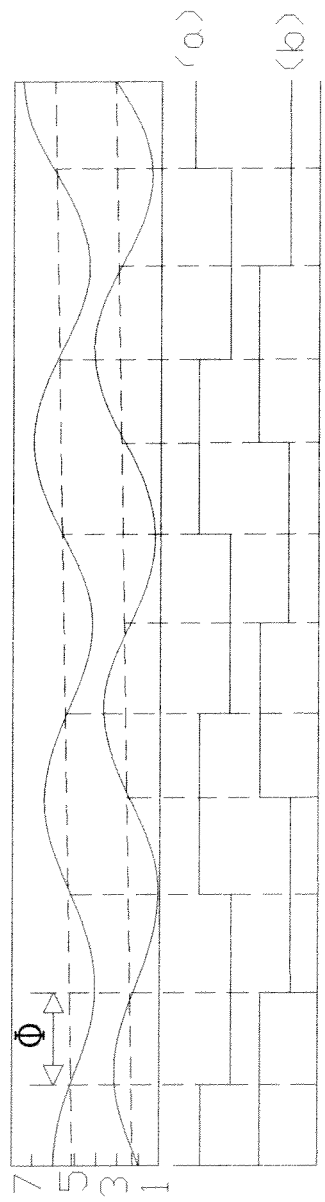
FIG. 1B is a schematic drawing showing waveforms of a reference beam and a signal beam of an embodiment according to the present invention.

Substitute simulation data into the equation (5) and (6) and signal waveforms are made by computational software, as shown in FIG. 1B(a). The signal is sent to a lock-in amplifier to measure phase change. Or by self-developed phase calculation algorithm to get the curve (b) in FIG. 1B. The phase change is calculated by counting in algorithms.

Figure 2:
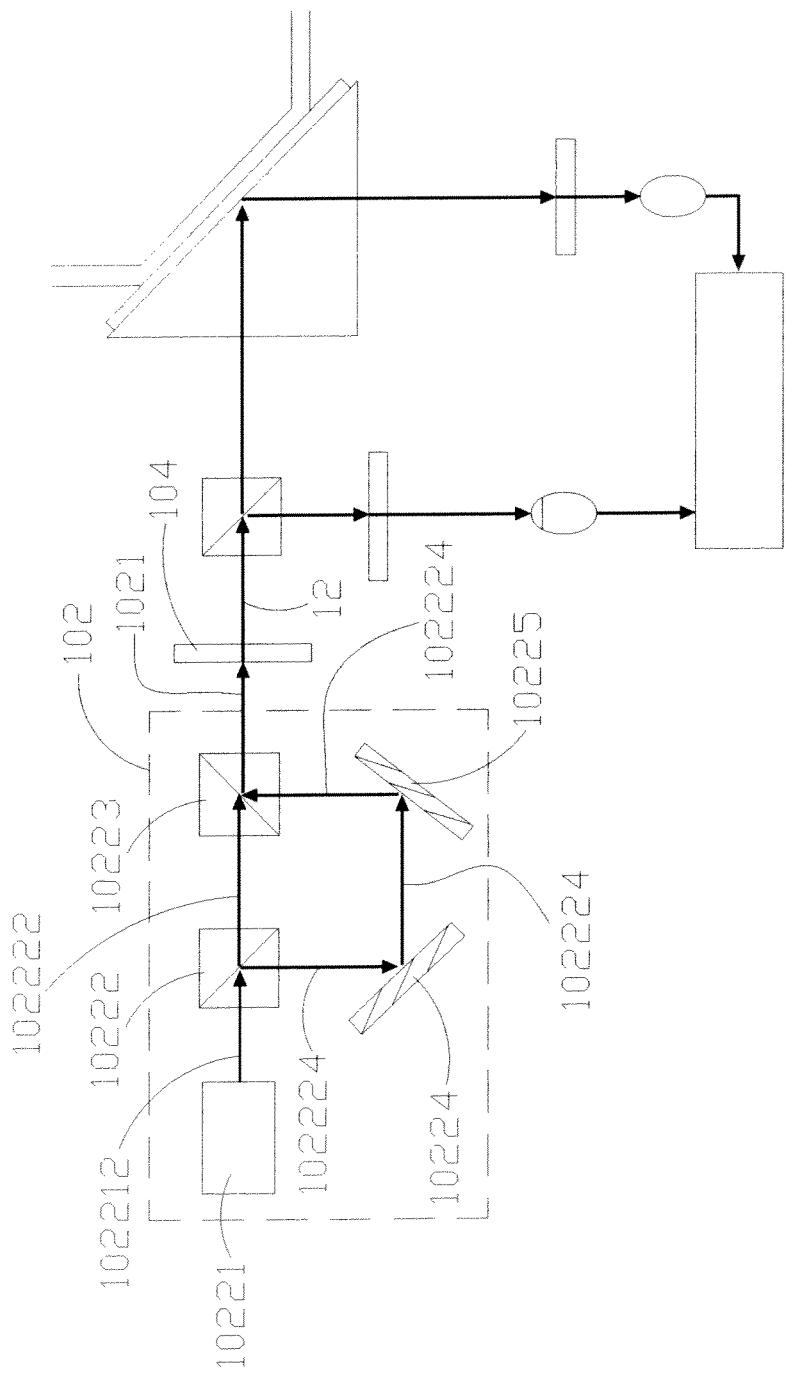
FIG. 2 is a schematic drawing showing structure of another embodiment of a SPR measuring device according to the present invention.

Refer to FIG. 2, another embodiment is disclosed. The difference between this embodiment and the above one is in the structure of the heterodyne light source 102. In this embodiment, the heterodyne light source 102 includes a wavelength-modulated light source 10221, a first polarization beam splitter 10222, a second polarization beam splitter 10223, a first reflector 10224, and a second reflector 10225. The wavelength-modulated light source 10221 produces an incident beam 102212 while the first polarization beam splitter 10222 splits the incident beam 102212 into a first transmitted beam 102222 and a first reflected beam 102224. The second polarization beam splitter 10223 recombines the first transmitted beam 102222 and the first reflected beam 102224 into a heterodyne light beam 1021. The first reflector 10224 reflects the first reflected beam 102224 to the second reflector 10225 and the second reflector 10225 reflects the first reflected beam 102224, already reflected by the first reflector 10224, to the second polarization beam splitter 10223. Thus the first transmitted beam 102222 and the first reflected beam 102224 are recombined to form the heterodyne light beam 1021 by the second polarization beam splitter 10223 and the heterodyne light beam 1021 is output to a phase retardation component 104 for being converted into a circularly polarized heterodyne light beam 12.

Figure 3:
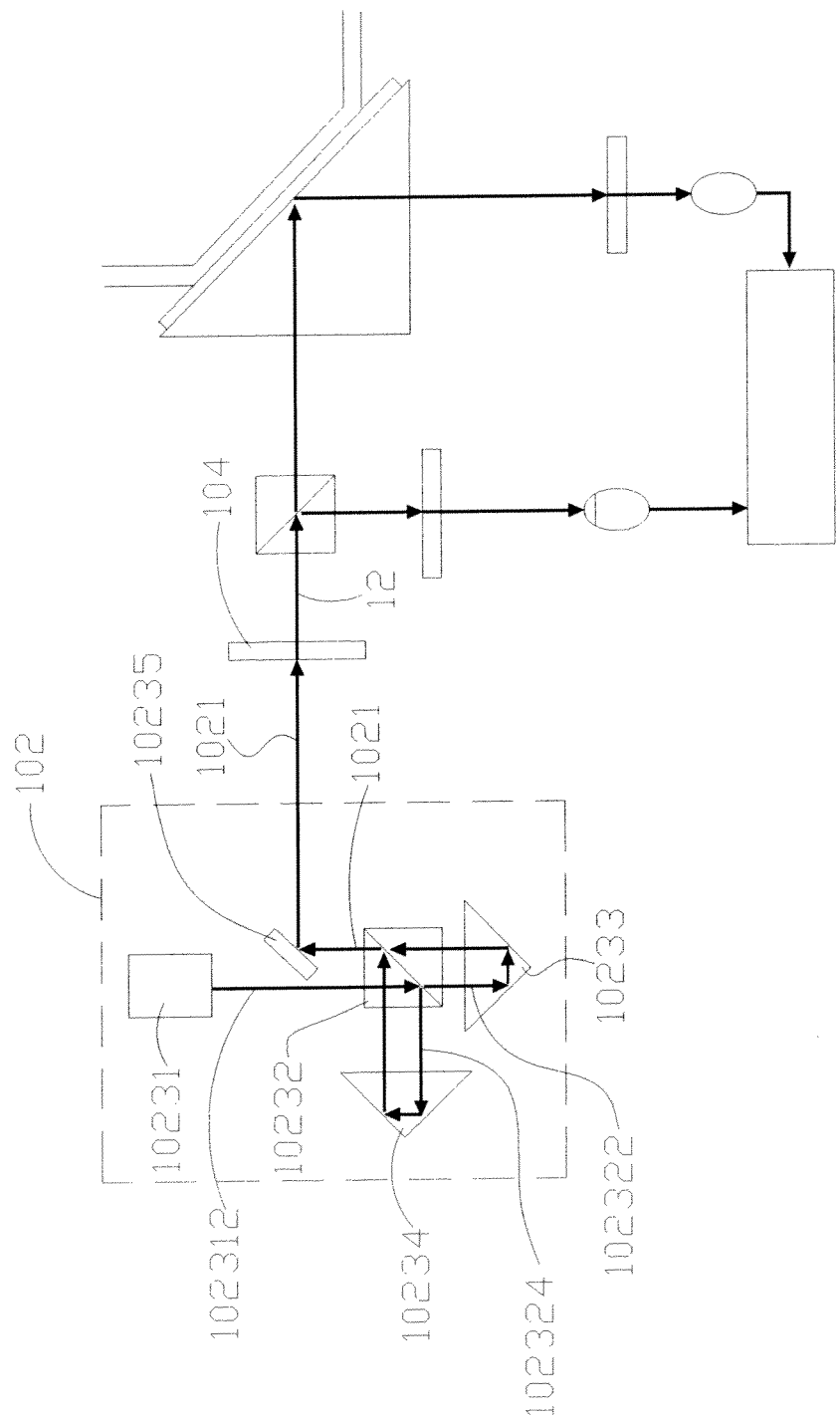
FIG. 3 is a schematic drawing showing structure of a further embodiment of a SPR measuring device according to the present invention.

Refer to FIG. 3, a further embodiment is revealed. The difference between this embodiment and the one in FIG. 1 is in the structure of the heterodyne light source 102. The heterodyne light source 102 of this embodiment consists of a wavelength-modulated light source 10231, a polarization beam splitter 10232, a first right angle prism 10233, and a second right angle prism 10234. The wavelength-modulated light source 10231 produces an incident beam 102312 while the polarization beam splitter 10232 splits the incident beam 102312 into a first transmitted beam 102322 and a first reflected beam 102324. The first right angle prism 10233 reflects the first transmitted beam 102322 to the polarization beam splitter 10232 and the second right angle prism 10234 reflects the first reflected beam 102324 to the polarization beam splitter 10232. The reflected first reflected beam 102324 and the reflected first transmitted beam 102322 are recombined into a heterodyne light beam 1021 by the polarization beam splitter 10232. In order to improve convenience of the heterodyne light beam 1021 in use (applications), this embodiment further includes a reflector 10235 that reflects the heterodyne light beam 1021 to a phase retardation component 104 so as to convert the heterodyne light beam 1021 into a circularly polarized heterodyne light beam 12.

Figure 4:
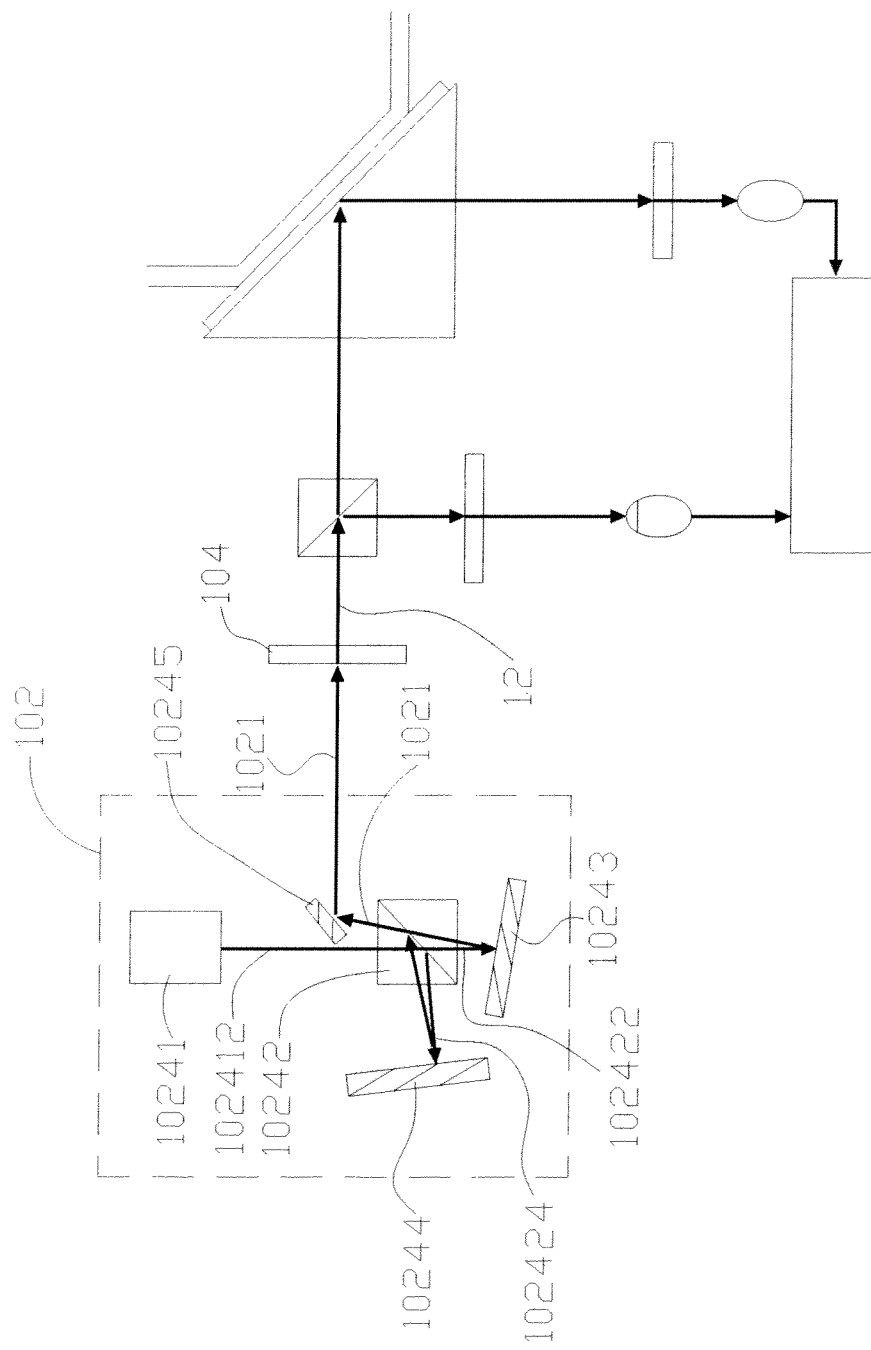
FIG. 4 is a schematic drawing showing structure of a further embodiment of a SPR measuring device according to the present invention.

Refer to FIG. 4, a further embodiment is revealed. The difference between this embodiment and the one in FIG. 1 is in the structure of the heterodyne light source 102. The heterodyne light source 102 of this embodiment is composed of a wavelength-modulated light source 10241, a polarization beam splitter 10242, a first reflector 10243, and a second reflector 10244. The wavelength-modulated light source 10241 produces an incident beam 102412 while the polarization beam splitter 10242 splits the incident beam 102412 into a first transmitted beam 102422 and a first reflected beam 102424. The first reflector 10243 reflects the first transmitted beam 102422 to the polarization beam splitter 10242 and the second reflector 10244 reflects the first reflected beam 102424 to the polarization beam splitter 10242. The reflected first reflected beam 102424 and the reflected first transmitted beam 102422 are recombined into a heterodyne light beam 1021 by the polarization beam splitter 10242. In order to improve convenience of the heterodyne light beam 1021 in use (applications), this embodiment further includes a third reflector 10245 that reflects the heterodyne light beam 1021 to a phase retardation component 104 so as to convert the heterodyne light beam 1021 into a circularly polarized heterodyne light beam 12.

Figure 5:
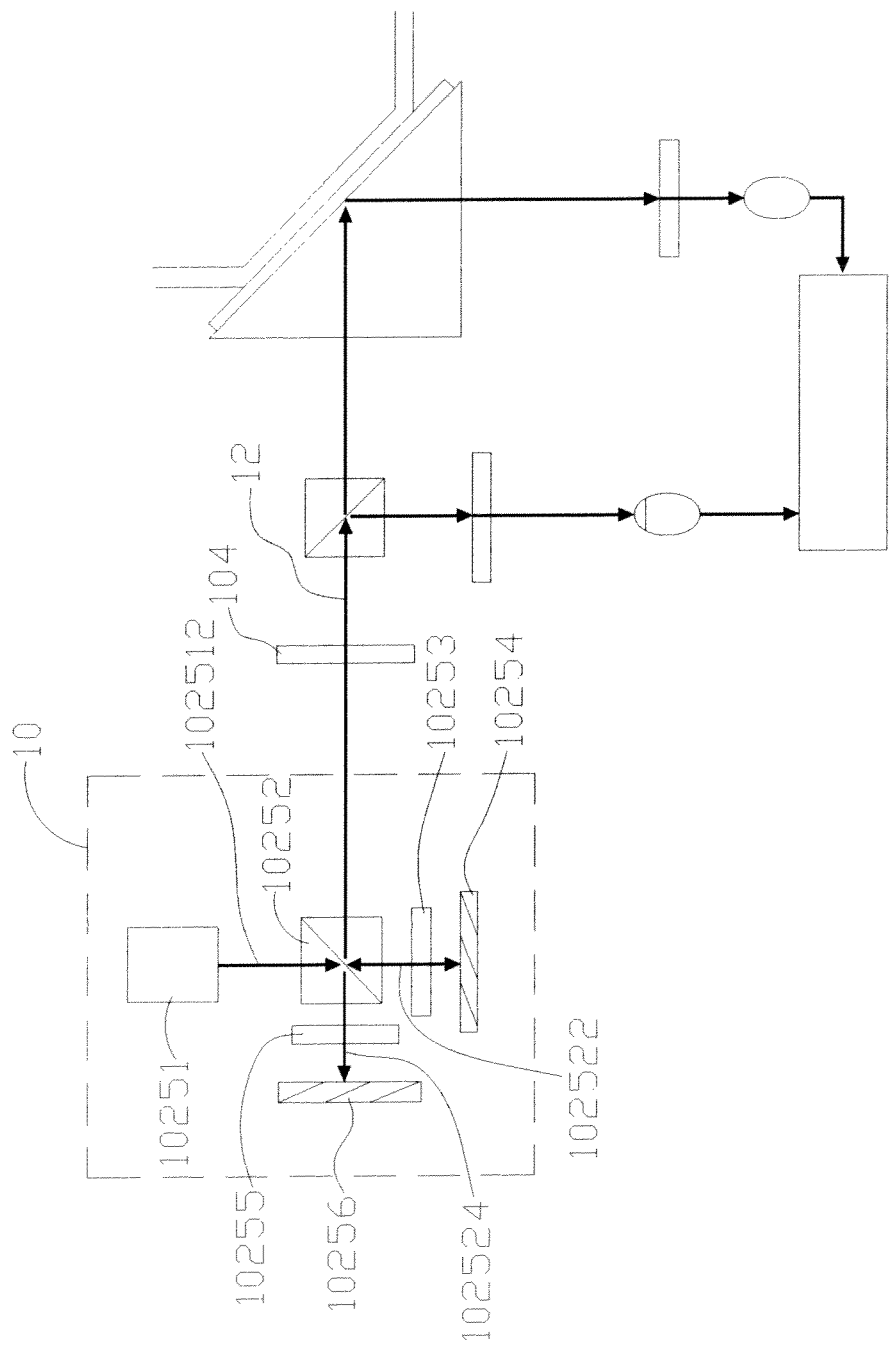
FIG. 5 is a schematic drawing showing structure of a further embodiment of a SPR measuring device according to the present invention.

Refer to FIG. 5, a further embodiment is revealed. The difference between this embodiment and the one in FIG. 1 is in the structure of the heterodyne light source 102. The heterodyne light source 102 of this embodiment consists of a wavelength-modulated light source 10251, a polarization beam splitter 10252, a first phase retardation component 10255, a first reflector 10256, a second phase retardation component 10253 and a second reflector 10254. The wavelength-modulated light source 10251 produces an incident beam 102512 while the polarization beam splitter 10252 splits the incident beam 102512 into a first transmitted beam 102522 and a first reflected beam 102524. The first phase retardation component 10255 retards the first reflected beam 102524. Both the first phase retardation component 10255 and second phase retardation component 10253 are quarter-wave plates. The first reflector 10256 reflects the polarized first reflected beam 102524 to the polarization beam splitter 10252. The second phase retardation component 10253 retards the first transmitted beam 102522 and the second reflector 10254 reflects the polarized first transmitted beam 102522 to the polarization beam splitter 10252. The polarized first reflected beam 102524 and the polarized first transmitted beam 102522 are recombined into a circularly polarized heterodyne light beam 12.

Figure 6:
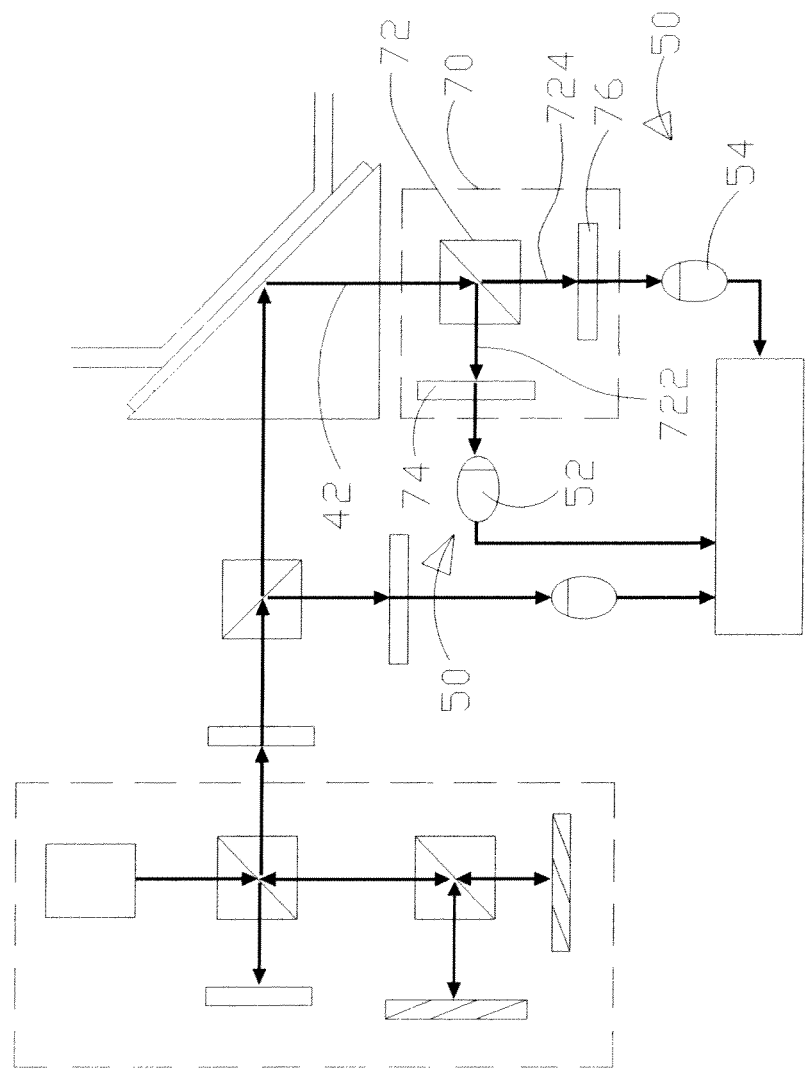
FIG. 6 is a schematic drawing showing structure of a further embodiment of a SPR measuring device according to the present invention.

Refer to FIG. 6, a further embodiment is revealed. As shown in the figure, the difference between this embodiment and the one in FIG. 1 is in that this embodiment includes an optical module 70. The optical module 70 receives the reflected signal beam 42 for amplifying the phase change of the reflected signal beam 42 and sends the reflected signal beam 42 to the second light sensing unit 50. The optical module 70 consists of a beam splitter 72, a first polarizer 74, and a second polarizer 76. The beam splitter 72 splits the reflected signal beam 42 into a first signal beam 722 and a second signal beam 724 while the first polarizer 74 polarizes the first signal beam 722 and the second polarizer 76 polarizes the second signal beam 724. The second light sensing unit 50 receives a first signal beam intensity of the polarized first signal beam 722 and a second signal beam intensity of the polarized second signal beam 724. The first polarizer 74 is a +45 degree polarizer while the second polarizer 76 is a −45 degree polarizer. The second light sensing unit 50 includes a first optical sensor 52 and a second optical sensor 54. The first optical sensor 52 receives the first signal beam intensity while the second optical sensor 54 receives the second signal beam intensity. Thus twice the phase change of the light signal of the reflected signal beam 42 after SPR is obtained and the sensitivity of the SPR measurement is increased.

In summary, the SPR measuring device of the present invention consists of a circularly polarized heterodyne light source, a beam splitting element, a first light sensing unit, a SPR sensor, a second light sensing unit, and a processing circuit. The circularly polarized heterodyne light source produces a circularly polarized heterodyne light beam while the beam splitter splits the circularly polarized heterodyne light beam into a reference beam and a signal beam. The first light sensing unit receives a reference light intensity of the reference beam. The SPR sensor receives the signal beam and reflects a reflected signal beam. The second light sensing unit receives a reflected light intensity of the reflected signal beam and the processing circuit calculates a phase difference between the reference light intensity and the reflected light intensity. By the circularly polarized heterodyne light beam, a phase change caused by SPR of an incident light is represented sensitively. Thus the convenience of measuring tiny changes in physical quantities of analytes is improved dramatically.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A SPR measuring device comprising:
   a circularly polarized heterodyne light source that produces a circularly polarized heterodyne light beam;
   a beam splitting element that splits the circularly polarized heterodyne light beam into a reference beam and a signal beam;
   a first light sensing unit that receives a reference light intensity of the reference beam;
   a SPR sensor that receives the signal beam and reflects a reflected signal beam;
   a second light sensing unit that receives a reflected light intensity of the reflected signal beam; and
   a processing circuit that calculates a phase difference between the reference light intensity and the reflected light intensity;
   wherein the circularly polarized heterodyne light source includes:
   a heterodyne light source produces a heterodyne light beam, the heterodyne light source includes:
      a wavelength-modulated light source that produces an incident beam;
      a beam splitter that splits the incident beam into a first transmitted beam and a first reflected beam;
      a light shielding element that receives the first reflected beam;
      a polarization beam splitter that splits the first transmitted beam into a second transmitted beam and a second reflected beam;
      a first reflector that reflects the second transmitted beam back to the polarization beam splitter; and
      a second reflector that reflects the second reflected beam back to the polarization beam splitter; the reflected second transmitted beam and the reflected second reflected beam are recombined to form the heterodyne light beam that is output through the beam splitter; and
   a phase retardation component that retards the heterodyne light beam to produce the circularly polarized heterodyne light beam.

2. The device as claimed in claim 1, wherein the phase retardation component is a quarter-wave plate.

3. The device as claimed in claim 1, wherein the heterodyne light source includes:
   a wavelength-modulated light source that produces an incident beam;
   a first polarization beam splitter that splits the incident beam into a first transmitted beam and a first reflected beam;
   a second polarization beam splitter that recombines the first transmitted beam and the first reflected beam into a heterodyne light beam; a first reflector that reflects the first reflected beam; and
   a second reflector that reflects the first reflected beam that has been reflected by the first reflector to the second polarization beam splitter.

4. The device as claimed in claim 1, wherein the heterodyne light source includes:
   a wavelength-modulated light source that produces an incident beam; a polarization beam splitter that splits the incident beam into a first transmitted beam and a first reflected beam;
   a first right angle prism that reflects the first transmitted beam to the polarization beam splitter; and
   a second right angle prism that reflects the first reflected beam to the polarization beam splitter; the reflected first reflected beam and the reflected first transmitted beam are recombined into a heterodyne light beam by the polarization beam splitter.

5. The device as claimed in claim 4, wherein the SPR measuring device further includes a reflector that reflects the heterodyne light beam.

6. The device as claimed in claim 1, wherein the heterodyne light source includes:
   a wavelength-modulated light source that produces an incident beam;

a polarization beam splitter that splits the incident beam into a first transmitted beam and a first reflected beam;

a first reflector that reflects the first transmitted beam to the polarization beam splitter; and a second reflector that reflects the first reflected beam to the polarization beam splitter; the reflected first reflected beam and the reflected first transmitted beam are recombined into a heterodyne light beam by the polarization beam splitter.

7. The device as claimed in claim 6, wherein the SPR measuring device further includes a third reflector that reflects the heterodyne light beam.

8. A SPR measuring device comprising:

a circularly polarized heterodyne light source that produces a circularly polarized heterodyne light beam;

a beam splitting element that splits the circularly polarized heterodyne light beam into a reference beam and a signal beam;

a first light sensing unit that receives a reference light intensity of the reference beam;

a SPR sensor that receives the signal beam and reflects a reflected signal beam;

a second light sensing unit that receives a reflected light intensity of the reflected signal beam; and a processing circuit that calculates a phase difference between the reference light intensity and the reflected light intensity;

wherein the circularly polarized heterodyne light source includes:

a wavelength-modulated light source that produces an incident beam;

a polarization beam splitter that splits the incident beam into a first transmitted beam and a first reflected beam;

a first phase retardation component that retards the first reflected beam;

a first reflector that reflects the polarized first reflected beam to the polarization beam splitter;

a second phase retardation component that retards the first transmitted beam; and a second reflector that reflects the polarized first transmitted beam to the polarization beam splitter; the polarized first reflected beam and the polarized first transmitted beam are recombined into the circularly polarized heterodyne light beam.

9. The device as claimed in claim 8, wherein the first phase retardation component is a quarter-wave plate.

10. The device as claimed in claim 8, wherein the second phase retardation component is a quarter-wave plate.

11. A SPR measuring device comprising:

a circularly polarized heterodyne light source that produces a circularly polarized heterodyne light beam;

a beam splitting element that splits the circularly polarized heterodyne light beam into a reference beam and a signal beam;

a first light sensing unit that receives a reference light intensity of the reference beam;

a SPR sensor that receives the signal beam and reflects a reflected signal beam;

a second light sensing unit that receives a reflected light intensity of the reflected signal beam; and a processing circuit that calculates a phase difference between the reference light intensity and the reflected light intensity;

wherein the SPR measuring device further includes an optical module that receives the reflected signal beam for amplifying phase change of the reflected signal beam and transmits the reflected signal beam to the second light sensing unit, the optical module includes:

a beam splitter that splits the reflected signal beam into a first signal beam and a second signal beam;

a first polarizer that polarizes the first signal beam; and a second polarizer that polarizes the second signal beam; the second light sensing unit receives a first signal beam intensity of the polarized first signal beam and a second signal beam intensity of the polarized second signal beam.

12. The device as claimed in claim 11, wherein the first polarizer is a polarizer for +45 degree polarization.

13. The device as claimed in claim 11, wherein the second polarizer is a polarizer for −45 degree polarization.

14. The device as claimed in claim 11, wherein the second light sensing unit includes:

a first optical sensor that receives the first signal beam intensity; and a second optical sensor that receives the second signal beam intensity.

* * * * *